(12) United States Patent
Mackool

(10) Patent No.: US 6,183,480 B1
(45) Date of Patent: Feb. 6, 2001

(54) INTRAOCULAR DEVICE FOR STABILIZING OF A LENS CAPSULE

(76) Inventor: Richard J. Mackool, 31-27 41st St., Astoria, NY (US) 11103

(*) Notice: Under 35 U.S.C. 154(b), the term of this patent shall be extended for 0 days.

(21) Appl. No.: 09/311,496

(22) Filed: May 13, 1999

Related U.S. Application Data

(60) Provisional application No. 60/128,836, filed on Apr. 9, 1999.

(51) Int. Cl.$^7$ ........................................... A61F 9/00
(52) U.S. Cl. ............................................ 606/107; 606/166
(58) Field of Search ........................... 606/166, 167, 606/107, 190, 206; 604/272; 623/4, 5, 6; 600/227, 236

(56) References Cited

U.S. PATENT DOCUMENTS

| | | |
|---|---|---|
| 4,573,998 | 3/1986 | Mazzocco . |
| 5,174,279 * | 12/1992 | Cobo et al. .................. 606/107 |
| 5,267,553 | 12/1993 | Graether . |
| 5,451,230 | 9/1995 | Steinert . |
| 5,514,076 * | 5/1996 | Ley ............................. 600/206 |
| 5,716,328 * | 2/1998 | Grieshaber et al. .......... 600/206 |
| 5,807,244 | 9/1998 | Barot . |
| 5,843,184 | 12/1998 | Cionni . |

* cited by examiner

Primary Examiner—Gary Jackson
Assistant Examiner—Anthony S. King
(74) Attorney, Agent, or Firm—Cobrin & Gittes

(57) ABSTRACT

A stabilizer and method of lens capsule retraction. The stabilizer includes a shaft, a stabilizing bend extending from the shaft, and a shank terminating at a termination end. The bend is between the shank and the shaft and is configured to provide a hook-like configuration. A distance between a trough of the stabilizing bend and the termination end is between 1.6 mm and 5.0 mm, preferably between 2.0 mm and 3.0 mm.

12 Claims, 2 Drawing Sheets

INTRAOCULAR DEVICE FOR STABILIZING OF A LENS CAPSULE

CROSS-REFERENCE TO RELATED PATENT APPLICATIONS

Provisional patent application Ser. No. 60/128,836, filed Apr. 9, 1999.

STATEMENT REGARDING FEDERALLY SPONSORED RESEARCH OR DEVELOPMENT

Not Applicable.

BACKGROUND OF THE INVENTION

1. Field of the Invention

The invention relates to devices that stabilize the lens capsule during or after cataract removal.

2. Discussion of Related Art

The clouding of the human eye is referred to as "cataract." Capsulorhexis involves tearing a generally circular opening (capsulotomy) through the anterior capsule of the capsular bag of the human lens. This opening or capsulotomy is bounded circumferentially by a continuous annular remnant edge of the anterior capsule, i.e., the edge is smooth and not jagged. During a cataract operation, the cataractous nucleus and cortex of the natural lens is removed from the capsular bag and an artificial lens implant is inserted into the bag through the capsulotomy.

Endocapsular tension rings are conventionally used to stabilize the lens capsule during cataract removal or after cataract removal. These rings consist of near circular plastic rings, which are inserted into the capsular sac that surrounds the human lens. These devices are currently used in the United States on an investigational basis and also abroad.

Iris retractors are used to enlarge the iris by retracting the same outwardly, thereby expanding the pupil, for the purpose of providing exposure of a cataract during cataract removal procedures. These retractors may be rigid or flexible, and each has an end configured into a hook. In particular, each has the characteristic of a relatively short shank length of approximately 1.0–1.25 mm, although there is a patent disclosure of a shank length between 1.0–1.5 mm. The shank length is the distance between the trough of the bend of the hook to the termination end of the hook's shank.

The inventor has used such iris retractors, which are used to retract the iris on a temporary basis, in an attempt to retract the lens capsule and has used them also to provide fixation to the lens capsule and enclosed cataract in numerous patients. However, the inventor found that such iris retractors provide non-constant fixation and frequently slip off the capsule so to render than unreliable for such use in retracting the lens capsule. Furthermore, such retractors do not restrain the peripheral regions of the capsule (the equatorial capsule). These regions are thus free to be attracted to various aspirating instruments used for cataract removal. The capsule may thus be easily damaged by such instruments.

BRIEF SUMMARY OF THE INVENTION

The present invention relates to a stabilizer or fixation device and method of lens capsule retraction. The stabilizer includes a shaft, a stabilizing bend extending from the shaft, and a shank terminating at a termination end. The bend is between the shank and the shaft and is configured to provide a hook-like configuration to the stabilizer. A distance between a trough of the stabilizing bend and the termination end is between 1.6 mm and 5.0 mm, preferably about 2.5 mm and between 2.0 mm and 3.0 mm.

BRIEF DESCRIPTION OF THE SEVERAL VIEWS OF THE DRAWING

For a better understanding of the present invention, reference is made to the following description and accompanying drawings, while the scope of the invention is set forth in the appended claims.

DETAILED DESCRIPTION OF THE INVENTION

Figure 1:
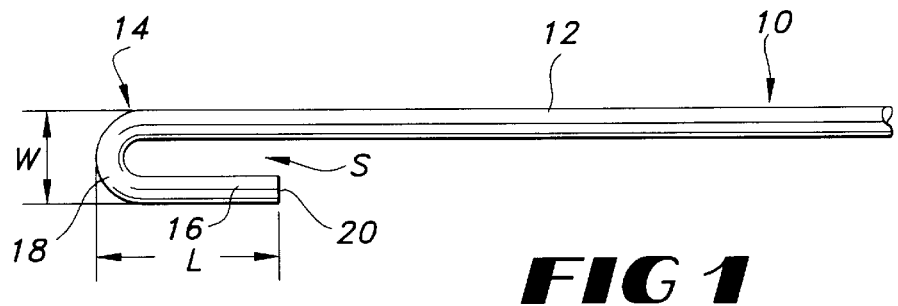
FIG. 1 is a perspective view of lens capsule stabilizer in accordance with a narrow variety embodiment of the invention.
Figure 2:
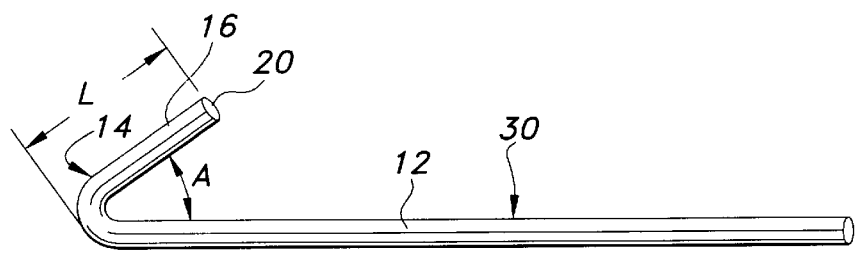
FIG. 2 is a perspective view of lens capsule stabilizer in accordance with a wide variety embodiment of the invention.

Turning to the drawing, FIG. 1 shows a narrow variety fixation device or stabilizer 10 and FIG. 2 shows a wide variety fixation device or stabilizer 30. Both stabilizers 10, 30, in accordance with the invention, share some common features.

Each includes a shaft 12, a stabilizing bend 14, and a shank 16. The stabilizing bend 14 has a trough 18 and the shank 16 terminates at a termination end 20.

The stabilizing bend 14 is between the shaft 12 and the shank 16 and changes a direction of orientation of the device 10 into a generally hook configuration. A length L, as measured between the trough 18 and the termination end 20, is between 1.6 mm and 5.0 mm, preferably between 2.0 mm and 3.0 mm. Such a length is desired so that the shank 16 extends to the capsular equator when in position.

In the case of the narrow variety stabilizer 10 of FIG. 1, preferably, the shaft 12 and shank 16 extend in a direction that is parallel or substantially parallel to each other. Further, a space S separates the shank 16 from the shaft 12 by an amount at least sufficient to fit the ocular tissue thickness at the boundary of the capsulotomy. Also, a width W between outer facing edges of the shaft 12 and shank 16 that face away from each other is within a range of 0.4 mm to 1.0 mm to fit while passing through confines of narrow incisions. Alternatively, the device may be made of a malleable material which permits it to temporarily collapse and deform during insertion through a small incision.

In the case of the wide variety stabilizer 30 of FIG. 2, the shaft 12 and the shank 16 are arranged to extend relative to each at an oblique angle A. The width between the outer facing edges of the shaft 12 and the shank 16 needs to be of a dimension that fits while passing through confines of conventional wide incisions.

A difference between the embodiments of FIGS. 1 and 2 is that in the case of the narrow variety embodiment of FIG.

1, the stabilizing bend 14 has a curvature configured to position the hook end 16 to extend in a direction substantially parallel to that of the shaft 12. Both the shaft 12 and the hook end 16 of the stabilizer 10 are straight. In the case of the wide variety embodiment of FIG. 2, the stabilizing bend 14 has a curvature configured to position the hook end 16 to extend at an oblique angle relative to the shaft 12. Both the shaft 12 and the hook end 16 are straight.

Figure 3:
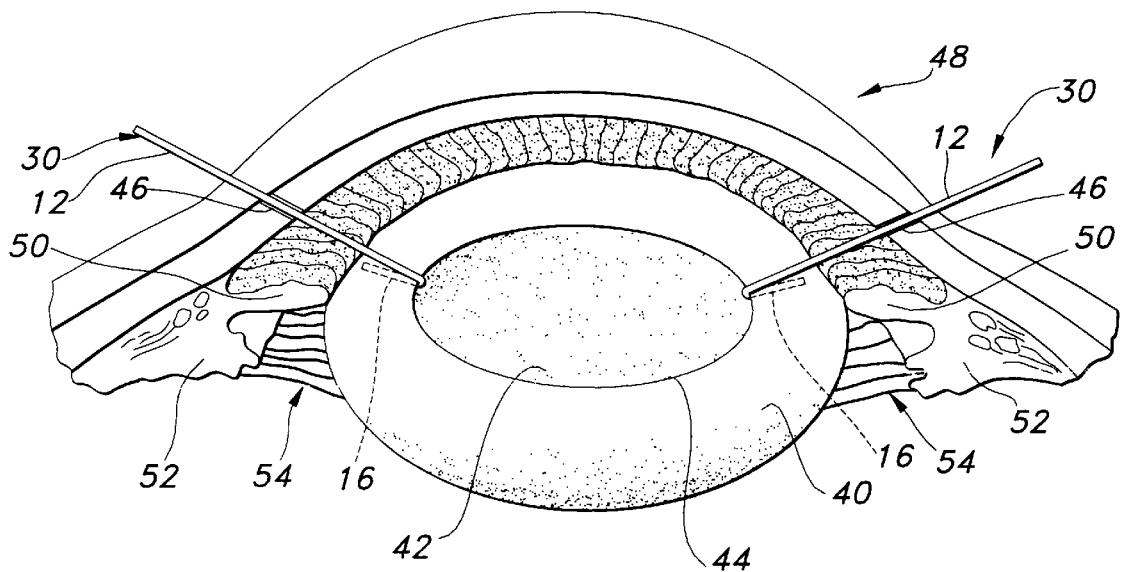
FIG. 3 is an oblique cut-away side view of the human eye illustrating the internal condition of the ocular area after cataract extraction and lens capsule stabilization in accordance with the present invention.

As shown in FIG. 3, the lens 42 is surrounded by a lens capsule 40. The lens capsule 40 is surgically cut in any medically safe conventional manner to form a conventional capsulotomy 44 or surgical opening during cataract removal and lens implantation procedures. The capsulotomy 44 has a continuous, unbroken edge forming its boundary and should not be jagged. Also shown are other components of the eye, such as the iris 50, ciliary body 52, and zonule 54.

The zonule 54 consists of numerous small fibers which course from the ciliary body 52 to the equatorial region of the lens capsule. The zonule 54 provides anatomic support for the lens capsule and contained lens, but may become weakened due to aging, trauma or a number of ocular disorders. When weakened, the zonule fails to provide adequate support to the capsule, and this may cause great difficulty during cataract surgery. For example, if not adequately restrained and supported, the capsule may be attracted to various aspirating instruments used during cataract removal and thereby damaged. Subsequent to this, portions of the cataract may fall through these damaged regions into the back or posterior portion of the eye, resulting in postoperative inflammation, glaucoma, additional procedures to retrieve and remove them, etc. As stated earlier, endocapsular tension rings are currently used to produce tension on the equatorial lens capsule either during and/or after cataract removal. When used during cataract removal, however, the inventor observed that these devices have certain disadvantages and shortcomings that are overcome by the use instead of the stabilizers 10 and 30 of the present invention.

The stabilizers 30 are arranged in a position to stabilize the lens capsule 40. The shanks 16 of the stabilizers 30 are shown in FIG. 3 to extend to the capsular equator.

The physician uses judgment to select either the narrow variety stabilizer 10 or the wide variety stabilizer 30 or both. The relative location and dimension of the incision 46 that the applicable stabilizer is to penetrate with respect to the boundary of the capsulotomy 44 may factor into which stabilizer is the more suitable one to use.

With the stabilizers in position such that the shank 16 is within the underside of the lens capsule 40 and the shaft 12 is outside of the lens capsule 40, the stabilizer 10, 30 is moved relative to the lens capsule until the bend 14 engages the boundary of the capsulotomy 44. For this reason, a distance S is critical to allow a portion of the lens capsule 40 that is adjacent the capsulotomy to fit within the space S. Any number of stabilizers 10, 30 may be used in this manner to firmly hold the boundary of the capsulotomy with the bend 14 and may apply pressure to the boundary to stabilize the lens capsule.

The amount of the pressure applied is roughly the same as that applied to retract the iris with iris retractors, but is exerted in accord with sound medical practice to avoid damaging the lens capsule. Once a sufficient amount of pressure is applied to stabilize so that the stabilizers 10, 30 are in their appropriate position, the stabilizers may be held in place at their shafts 12 with the same type of holders that hold iris retractors in place.

Figure 4:
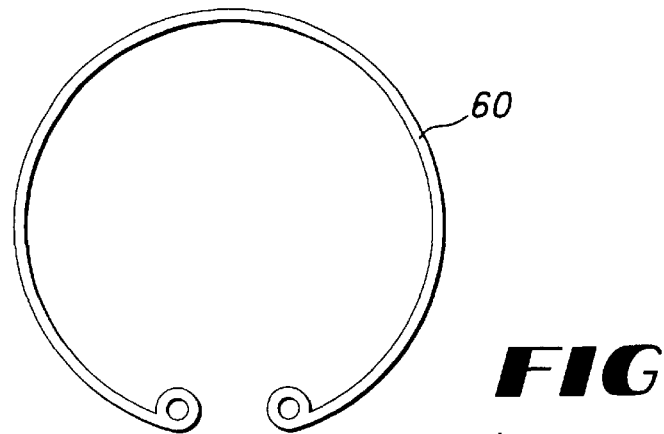
FIG. 4 is a plan view of a conventional endocapsular tension ring used to stabilize the lens capsule and having a diameter of approximately 12 mm.

FIG. 4 shows a conventional capsular tension ring 60 used to stabilize the lens capsule during or after cataract removal. Such a ring 60 is no longer needed during cataract removal in accordance with the use of the stabilizers 10, 30 of the present invention, which stabilize the cataract and the surrounding lens capsule during removal of the cataract. U.S. Pat. No. 5,843,184, entitled ENDOCAPSULAR TENSION RING AND METHOD OF IMPLANTING THE SAME, reveals an exemplary endocapsular tension ring.

In addition, the stabilizers 10, 30 provide greater stability to the lens capsule 40 of FIG. 3 and the enclosed cataract than does the capsular tension ring 60. This is because the endocapsular tension ring provides only an outward force on the lens capsule, but provides no support for the capsule and enclosed cataract. The capsule and the enclosed cataract are therefore not prevented from shifting downward toward the back of the eye, nor are they prevented from undesirably rotating during the process of cataract removal. Such downward shifting or rotation adds greatly to the difficulty of cataract removal, and further weakens the attachments (zonule) of the lens capsule to the ciliary body. The stabilizers 10, 30 of the present invention simultaneously support the capsule and enclosed cataract and restrict rotation of the capsule caused by torsional forces which are routinely applied to the enclosed cataract by the surgical instruments used for cataract removal.

Furthermore, endocapsular tension rings have the disadvantage of trapping cataractous lens material (lens cortex) between themselves and the peripheral regions of the capsule against which they exert pressure. This makes lens cortex removal much more difficult and adds to the trauma of the procedure. The stabilizers 10, 30 of the present invention do not trap lens cortex in any manner. Such was observed by the inventor, who has performed literally tens of thousands of cataract operations.

Indeed, the inventor found that the stabilizers 10, 30 of FIGS. 1 and 2 permit the lens capsule 40 of FIG. 3 to become hooked and firmly held so as to provide support to the capsular equator, following the creation of the circular surgical opening in the lens capsule commonly called the capsulotomy 44. Preferably, by arranging multiple stabilizers each constructed in accordance with that of either FIGS. 1 or 2, the lens becomes stabilized.

The present inventor observed that such stabilizers of the embodiments of FIGS. 1 and 2 should have a length of the shank 16 between 1.6 mm and 5.0 mm, preferably between 2.0 mm and 3.0 mm, as measured between the trough 18 of the stabilizing bend 14 and the termination of the hook end 16. A shank length of about 2.5 mm or exactly 2.5 mm is satisfactory. Such stabilizers 10, 30 having such a length have never been used previously in connection with any eye surgical procedure as far as the inventor is aware, because they have no perceived usefulness in the field.

A conventional stabilizer with a shank length between 1.0 mm and 1.25 mm has been used by the present inventor in an effort to stabilize the lens capsule. The present inventor found the use of multiple ones of them to be unreliable in that they frequently slip off the capsule and provide non-constant fixation because of their short shank length. Such stabilizers are typically used as iris retractors 70 in the manner shown in FIGS. 5 and 6 to retract the iris 46 on a temporary basis.

Figure 6:
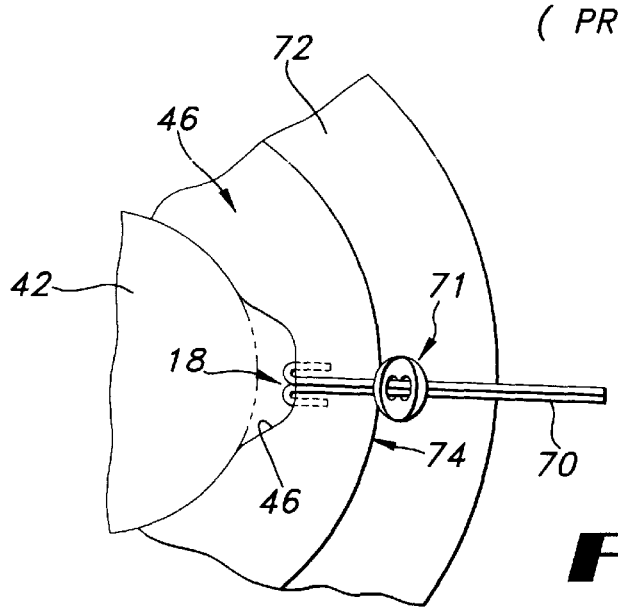
FIG. 6 is a plan view of conventional iris retractor in position retracting the iris.

The shafts of the iris retractors 70 are each held in position by a holder 71, which may be a resilient material having two openings that align with each while the resilient material is bent to accommodate insertion of the shaft through both openings. The resilient material need only be squeezed to permit its relative movement along the length of the shaft. Also shown in FIG. 6 is the sclera 72 and the transition 74 between the iris and the sclera 72.

Figure 5:
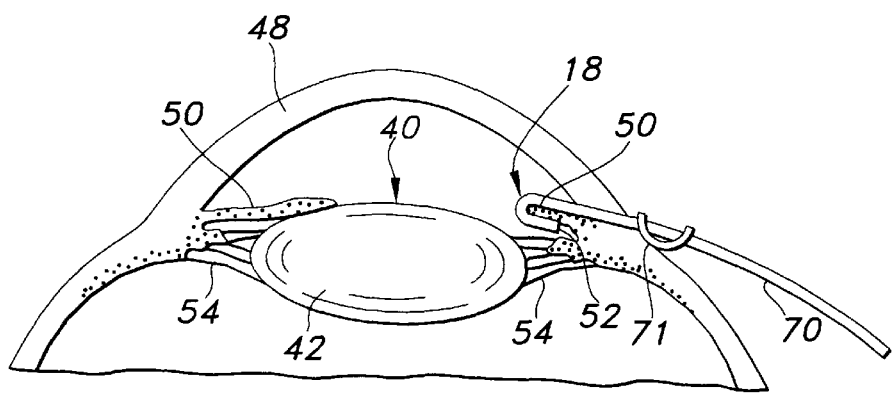
FIG. 5 is a cut-away side view of a conventional iris retractor used to retract the iris.

The stabilizer 10, 30 of the embodiments of FIGS. 1 and 2 may be made of the same materials as a conventional retractor 70 of FIG. 5 and may be either flexible or rigid. Such a conventional iris retractor is revealed in U.S. Pat. No. 5,716,328, whose contents are incorporated herein by reference as concerns its disclosure of materials of the iris retractor and manner of manufacture of the same.

The phrase "about 2.5 mm" means 2.5 mm plus or minus 0.2 mm. The phrases "between 1.6 mm and 5.0 mm" and "between 2.0 mm and 3.0 mm)" are inclusive of the endpoints of these ranges. The shaft length is many multiple times the length of the shank. Further, the shank, bend and shank need to be sterilized to minimize the risk of contamination when in use. The phrase "enclosed cataract" refers to the cataractous lens material that is contained within the lens capsule.

While the foregoing description and drawings represent the preferred embodiments of the present invention, it will be understood that various changes and modifications may be made without departing from the spirit and scope of the present invention.

What is claimed is:

1. An intraocular device to stabilize ocular tissue during and after removal of a cataract comprising an elongated shaft, a bend, and an elongated shank, the bend being arranged between the shaft and the shank and defining a trough and configured so that a length between the trough and a termination end of the shank is between 1.6 mm and 5.0 mm, the shaft being longer than said shank, said shaft and said shank being spaced from each other, whereby said intraocular device is for stabilizing ocular tissue during and after removal of a cataract.

2. A device as in claim 1, wherein the length is between 2.0 mm and 3.0 mm.

3. A device as in claim 1, wherein the length is about 2.5 mm.

4. A device as in claim 1, wherein the shank extends in a linear manner from the bend to the termination, the bend defining an oblique angle between the shaft and the shank.

5. A device as in claim 1, wherein the shaft, the bend and the shank are in a sterilized condition.

6. A device as in claim 1, wherein the shank extends in a linear manner from the bend to the termination, the bend defining an angle between the shaft and the shank such that the shaft and the shank extend substantially parallel with each other.

7. A method of stabilizing an ocular tissue during and after removal of the cataract, the eye having a lens capsule with a capsulotomy whose periphery defines a surgical opening in a lens capsule of the eye, the eye having a cornea with a periphery having an incision, the method comprising the steps of:

arranging an elongated shaft of a stabilizer to penetrate through the incision from outside the cornea, the stabilizer being configured to stabilize the lens capsule; and hooking a margin of the capsulotomy in a lens capsule with the stabilizer to stabilize the lens capsule, the stabilizer having a bend arranged between the shaft and an elongated shank of the stabilizer, the shaft and the shank being spaced from each other, the bend having a trough, the shank having a termination end arranged so that a distance between the trough and the termination end is between 1.6 and 5.0 mm.

8. A method as in claim 7, wherein the length is between 2.0 mm and 3.0 mm.

9. A method as in claim 7, wherein the length is about 2.5 mm.

10. A method as in claim 7, wherein the shank extends in a linear manner from the bend to the termination, the bend defining an oblique angle between the shaft and the shank.

11. A method as in claim 7, wherein the shank extends in a linear manner from the bend to the termination, the bend defining an angle between the shaft and the shank such that the shaft and the shank extend substantially parallel with each other.

12. A method as in claim 7, wherein the shaft, the bend and the shank are each in a sterilized condition before penetration through the incision.

* * * * *